(12) United States Patent
Shur et al.

(10) Patent No.: US 7,868,399 B2
(45) Date of Patent: Jan. 11, 2011

(54) SEMICONDUCTOR SENSING DEVICE

(75) Inventors: Michael Shur, Latham, NY (US);
Remigijus Gaska, Columbia, SC (US);
Yuriy Bilenko, Centereach, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 444 days.

(21) Appl. No.: 12/106,597

(22) Filed: Apr. 21, 2008

(65) Prior Publication Data

US 2008/0224148 A1    Sep. 18, 2008

Related U.S. Application Data

(63) Continuation of application No. 10/721,803, filed on Nov. 25, 2003, now Pat. No. 7,382,004.

(51) Int. Cl.
*H01L 23/58* (2006.01)

(52) U.S. Cl. .............................. 257/414; 257/E31.093; 438/235

(58) Field of Classification Search ................. 257/183, 257/184, 192, 197, E32.021, E31.093, 414; 438/46, 180, 235
See application file for complete search history.

(56) References Cited

U.S. PATENT DOCUMENTS

| 4,180,771 | A | 12/1979 | Guckel |
|---|---|---|---|
| 4,592,824 | A | 6/1986 | Smith et al. |
| 5,200,633 | A | 4/1993 | Dickert et al. |
| 5,874,047 | A | 2/1999 | Schoning |
| 6,521,109 | B1 | 2/2003 | Bartic et al. |
| 7,017,389 | B2 | 3/2006 | Gouma |
| 2002/0045272 | A1 | 4/2002 | McDevitt et al. |
| 2003/0132392 | A1 | 7/2003 | Kuroda et al. |

FOREIGN PATENT DOCUMENTS

DE    10032062 A1    1/2002

OTHER PUBLICATIONS

J. Schalwig et al.; Gas sensitive GaN/AlGaN-heterostructures; Sensors and Actuators B 87; 2002; pp. 425-430.
R.P. Buck et al.; Measurement of pH Definition, standards, and procedures; IUPAC, Pure and Applied Chemistry 74; 2002; pp. 2169-2200.

*Primary Examiner*—Thomas L Dickey
*Assistant Examiner*—Fazli Erdem
(74) *Attorney, Agent, or Firm*—John W. LaBatt; Hoffman Warnick LLC

(57) ABSTRACT

A semiconductor sensing device in which a sensing layer is exposed to a medium being tested in an area below and/or adjacent to a contact. In one embodiment, the device comprises a field effect transistor in which the sensing layer is disposed below a gate contact. The sensing layer is exposed to the medium by one or more perforations that are included in the gate contact and/or one or more layers disposed above the sensing layer. The sensing layer can comprise a dielectric layer, a semiconductor layer, or the like.

17 Claims, 2 Drawing Sheets

SEMICONDUCTOR SENSING DEVICE

REFERENCE TO RELATED APPLICATION

The current application is a continuation of U.S. Utility patent application Ser. No. 10/721,803, titled "Semiconductor sensing device", which was filed on 25 Nov. 2003 now U.S. Pat. No. 7,382,004, and which is hereby incorporated by reference.

BACKGROUND OF THE INVENTION

1. Technical Field

The invention relates generally to sensors, and more specifically, to a semiconductor sensing device.

2. Related Art

Sensors, such as pH sensors for chemicals, have been successfully developed for many years. Each sensor includes a sensing element that generates a signal (e.g., visual, audio, electrical, etc.) in response to the presence/absence of a property and/or a level of the property in a medium (e.g., a liquid, a chemical, etc.) being tested. For example, a pH sensor can generate a signal that is based on an ion concentration and polarity of the medium.

In a semiconductor configured to sense a property of a medium, the sensing element can generate an electrical signal based on a property of the medium being tested. The sensing element can be connected to a circuit for transferring and/or transforming the electrical signal that is generated by the sensing element. Typically, the sensing element is constructed so that one end tests the medium, while the other end contacts the circuit. However, using this approach, the sensing element, its connection to the medium, and/or its connection to the circuit may deteriorate over time, multiple uses, etc.

Another semiconductor approach for sensing a medium property incorporates a pore network on the surface of a silicon body of the semiconductor. This approach enables the accommodation and anchorage of material sensitive to the property. However, it does not eliminate the necessity of incorporating an additional property-sensitive substance into the semiconductor.

Sensors based on compound semiconductors have also been proposed. For example, a GaN-AlGaN heterostructure can be used as a semiconductor base of a gas sensor. The gas sensor can include two planar electrodes separated by an additional property-sensitive layer on the surface of the semiconductor. In this approach, the heterostructure enhances the polarization of the surface under the sensing element, thereby increasing the sensor signal. However, this approach also requires an additional property sensing element.

As a result, a need exists for an improved semiconductor sensing device for sensing a property of a medium. In particular, a need exists for a semiconductor sensing device that can operate without the requirement of modifying and/or repairing the additional sensing elements. Further, a need exists for a semiconductor sensing device that provides a reliable transformation of the medium property being sensed, e.g., ion polarity, ion concentration, or the like into an electrical signal.

SUMMARY OF THE INVENTION

The invention provides an improved semiconductor sensing device. Specifically, under the present invention, a semiconductor device includes a sensing layer incorporated below a contact. The sensing layer is exposed to a medium being tested in an area below and/or adjacent to the contact. For example, the contact can comprise a gate contact in a field effect transistor. The gate contact can include one or more perforations that allow the medium to contact the sensing layer below the gate contact. Perforations can also be included in one or more layers that are disposed above the sensing layer. In this manner, the device operation will be altered based on the property of the medium, thereby providing an indication of the presence/absence and/or level of the property in the medium.

A first aspect of the invention provides a semiconductor device configured to sense a property of a medium, the device comprising: a contact; and a sensing layer disposed below the contact, wherein the sensing layer is exposed to the medium in an area below the contact.

A second aspect of the invention provides a field effect transistor (FET) configured to sense a property of a medium, the FET comprising: a source contact; a drain contact; a gate contact, wherein the gate contact defines a gate area disposed below and adjacent the gate contact; and a sensing layer for sensing the property, wherein the sensing layer is disposed below the gate contact and wherein the sensing layer is exposed to the medium in the gate area.

A third aspect of the invention provides a semiconductor device configured to sense a property of a medium, the device comprising: a contact that includes at least one perforation to expose a sensing layer to the medium; a dielectric layer disposed below the contact; and an active structure disposed below the dielectric layer, wherein the sensing layer comprises at least one of: the dielectric layer and a semiconductor layer in the active structure.

The illustrative aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

It is understood, that for purposes of this description Al means Aluminum, Ga means Gallium, N means Nitrogen, In means Indium, Si means Silicon, O means Oxygen, and C means Carbon. Further, it is understood that "group III elements" comprise the elements Al, Ga, In, Boron (B), and Thallium (Tl).

As indicated above, the invention provides an improved semiconductor sensing device. Specifically, under the present invention, a semiconductor device includes a sensing layer incorporated below a contact. The sensing layer is exposed to a medium being tested in an area below and/or adjacent to the contact. For example, the contact can comprise a gate contact in a field effect transistor. The gate contact can include one or more perforations that allow the medium to contact the sensing layer below the gate contact. Perforations can also be included in one or more layers that are disposed above the sensing layer. In this manner, the device operation will be altered based on the property of the medium, thereby providing an indication of the presence/absence and/or level of the property in the medium.

Figure 1:
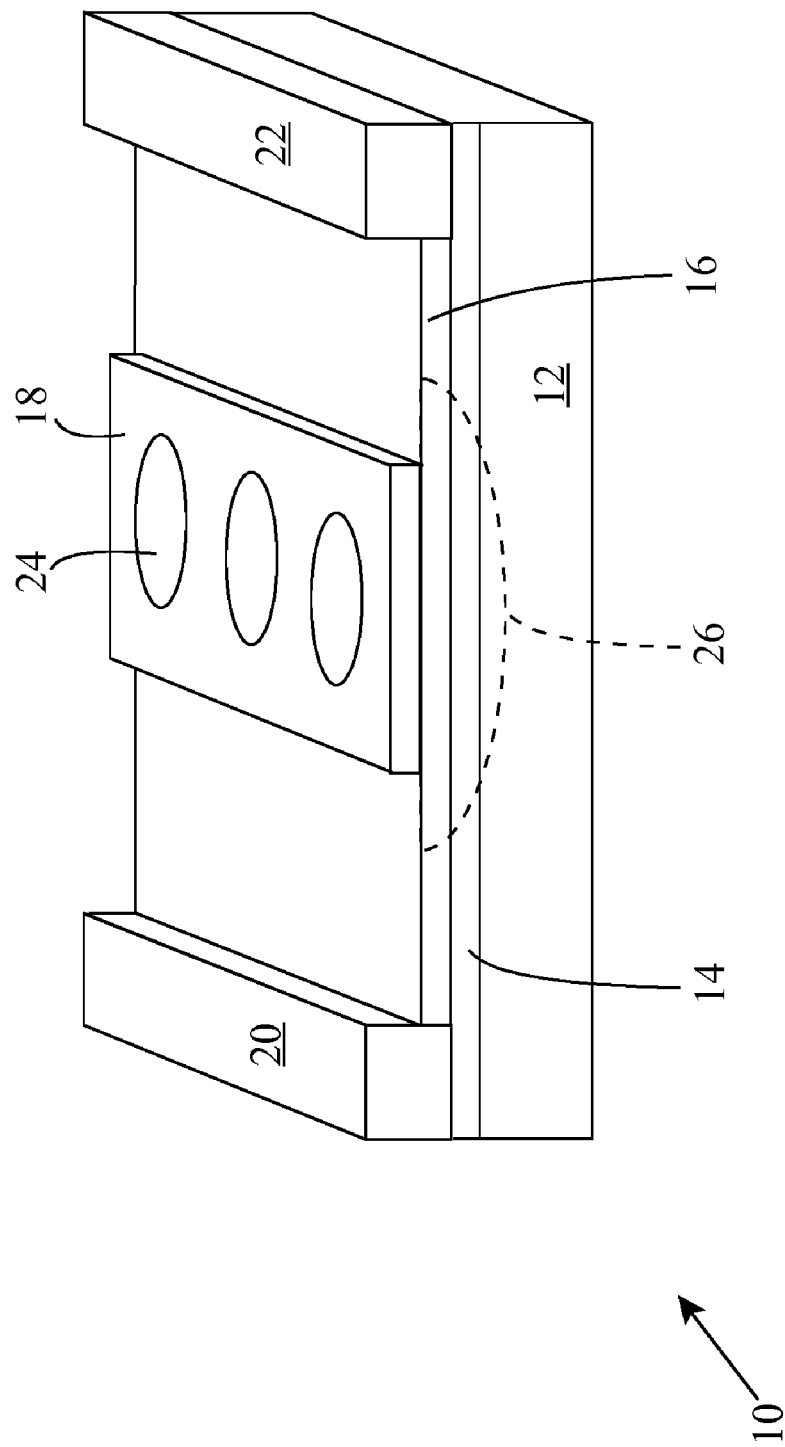
FIG. 1 shows an illustrative semiconductor sensing device according to one embodiment of the invention.

Turning to the drawings, FIG. 1 shows an illustrative semiconductor sensing device 10 according to one embodiment of the invention. Device 10 is shown including a substrate 12, an active structure 14 disposed above substrate 12, and a dielectric layer 16 disposed above active structure 14. Device 10 can include any type of substrate 12. For example, substrate 12 can comprise sapphire, silicon carbide (SiC), spinel, silicon, bulk GaN, bulk AlN, or bulk AlGaN. Active structure 14 can comprise any combination of one or more layers, e.g., a heterostructure, that provide the desired functionality for device 10. Dielectric layer 16 can comprise, for example, one or more layers of $SiO_2$, and/or SiN. However, it is understood that inclusion of dielectric layer 16 in device 10 is optional. In one embodiment, active structure 14 comprises an AlGaN/GaN heterostructure with a GaN layer acting as the sensing layer.

It is understood that each layer (and structure) shown in device 10 can be deposited directly on an adjacent, lower layer or one or more additional layers can be formed between the two adjacent layers shown. The composition and configuration of any additional layers and/or components can vary depending on the desired functionality of device 10 and/or any improvements made to enhance the operation and/or reliability of device 10. Further, each layer can be formed over all or only a portion of a lower layer, can vary in thickness, and can be formed into any pattern that provides the desired functionality for device 10. Each layer can be deposited and/or patterned using any solution now known or later developed. For example, each nitride-based layer can be formed using Molecular Beam Epitaxy (MBE), Metal Organic Chemical Vacuum Deposition (MOCVD), and/or patterned using selective etching.

As shown, device 10 can be configured to operate as a field effect transistor (FET). To this extent, device 10 is shown including a gate contact 18 disposed above dielectric layer 16, a source contact 20, and a drain contact 22. Each contact 18, 20, 22, can be formed using any solution now known or later developed. In order to sense a property of a medium, device 10 is also configured so that its operation changes based on the property of the medium.

In one embodiment, a sensing layer is exposed to the medium being tested in a gate area 26 of device 10. As shown in FIG. 1, gate area 26 comprises a portion of device 10 disposed below and/or adjacent gate contact 18. As is known in the art, gate area 26 is determined by the spreading of the gate-created electrical potential. Gate contact 18 is shown including a set (one or more) of perforations 24. Perforations 24 allow the medium to contact the sensing layer in the area below gate contact 18. The size and/or number of each perforation 24 can be adjusted to adjust the total area of the sensing layer that is exposed to the medium. In one embodiment, each perforation 24 exposes an area in the range of approximately one square nanometer to approximately ten square centimeters. While shown as having an elliptical shape, it is understood that each perforation 24 can comprise any desired shape.

As noted, the sensing layer is exposed to the medium in gate area 26. For example, the sensing layer can comprise dielectric layer 16. In this case, perforations 24 would extend through gate contact 18 to allow the portion of dielectric layer 16 below gate contact 18 to contact the medium. Alternatively, the sensing layer could comprise one or more layers in active structure 14, e.g., a semiconductor layer. In this case, one or more perforations 24 could extend through gate contact 18, dielectric layer 16 (if present), and/or any other layers disposed above the sensing layer.

In any event, the sensing layer is electrically sensitive to changes in the electrical characteristics within gate area 26. As a result, exposing the sensing layer to the medium in gate area 26 will alter an electrical potential on gate contact 18. Consequently, the output of device 10 will produce an amplified response to any changes to the sign and/or amount of electrical charge in the medium. This response can be used to measure, for example, hydrogen ion concentration or pH.

Figure 2:
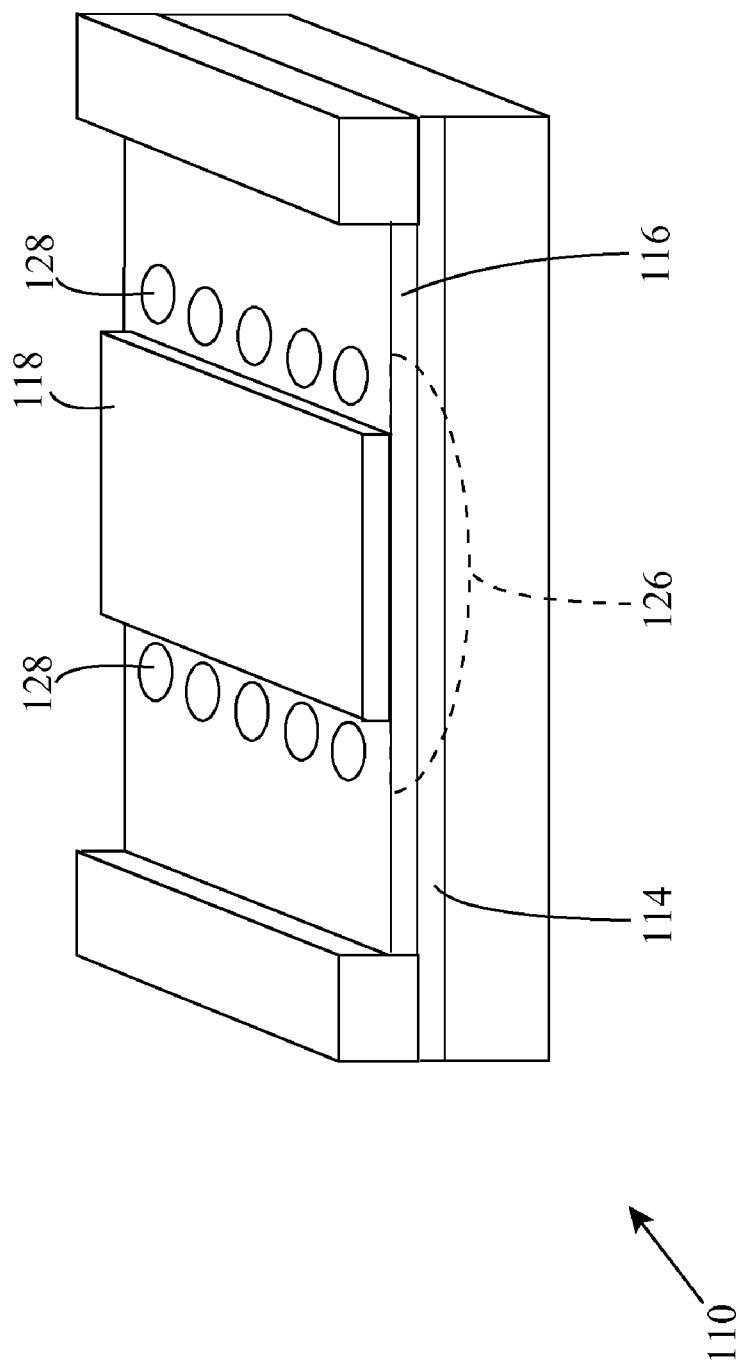
FIG. 2 shows an illustrative semiconductor sensing device according to another embodiment of the invention.

FIG. 2 shows an alternative semiconductor sensing device 110 according to another embodiment of the invention. In this case, one or more layers in active structure 114 can comprise the sensing layer. In order to expose the sensing layer(s) to a medium in gate area 126, dielectric layer 116 is shown including a set of perforations 128 that are adjacent gate contact 118. Each perforation 128 passes through dielectric layer 116 and/or any additional layers in active structure 114 to expose the sensing layer(s) to the medium. It is understood that gate contact 118 could also include perforations that expose portions of the sensing layer directly below gate contact 118 to the medium as shown in FIG. 1.

In one embodiment, device 10 can comprise a compound semiconductor FET. In this case, device 10 would present polarization effects in the bulk and on the surface. These effects can be enhanced when a heterostructure such as AlGaN/GaN and quantum wells are used to form active structure 14. It is understood that various types of semiconductor FETs could be used. For example, device 10 can comprise a silicon metal-oxide-semiconductor FET (MOSFET), a GaN-based semiconductor FET, a metal semiconductor FET (MESFET), a metal-insulator-semiconductor (MISFET), or the like.

The foregoing description of various embodiments of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A semiconductor device configured to sense a property of a medium, the device comprising:
    a sensing layer;
    a dielectric layer directly on the sensing layer; and
    an electrical contact directly on the dielectric layer, wherein the contact defines a contact area disposed below and adjacent to the contact, wherein the dielectric layer extends beyond the contact area, and wherein the sensing layer is exposed to the medium in the contact area by at least one perforation in the dielectric layer.

2. The device of claim 1, wherein the at least one perforation includes at least one perforation that extends through the contact and the dielectric layer.

3. The device of claim 1, wherein the at least one perforation includes at least one perforation in the contact area adjacent to the contact.

4. The device of claim 1, wherein the property comprises a pH level.

5. The device of claim 1, wherein the dielectric layer includes at least one perforation in the contact area for exposing the sensing layer to the medium.

6. The device of claim 1, wherein the sensing layer comprises a nitride active structure.

7. A semiconductor device configured to sense a property of a medium, the device comprising:
   a nitride active structure, wherein the nitride active structure contributes to electronic functionality of the device;
   a dielectric layer directly on the nitride active structure; and
   an electrical contact directly on the dielectric layer, wherein the electrical contact includes at least one perforation to expose a sensing layer to the medium in an area below the electrical contact, and wherein the sensing layer comprises at least one of: the dielectric layer or a semiconductor layer in the active structure.

8. The semiconductor device of claim 7, wherein the sensing layer comprises the semiconductor layer and wherein the dielectric layer includes the at least one perforation.

9. The semiconductor device of claim 8, wherein the dielectric layer further includes at least one perforation in the contact area adjacent to the contact for exposing the sensing layer to the medium.

10. The semiconductor device of claim 7, wherein the dielectric layer extends beyond a contact area disposed below and adjacent to the contact.

11. A method of sensing a property of a medium, the method comprising:
    exposing a sensing layer in a semiconductor device to the medium, the semiconductor device including:
      a nitride active structure, wherein the nitride active structure contributes to electronic functionality of the device;
      a dielectric layer directly on the nitride active structure; and
      an electrical contact directly on the dielectric layer, wherein the electrical contact includes at least one perforation to expose a sensing layer to the medium in an area below the electrical contact, and wherein the sensing layer comprises at least one of: the dielectric layer or a semiconductor layer in the active structure;
    detecting a response in an output of the device to the medium; and
    measuring the property based on the response.

12. The method of claim 11, wherein the property is a pH level.

13. The method of claim 11, wherein the device is a field effect transistor (FET).

14. The method of claim 13, the device further including a source contact and a drain contact, wherein the dielectric layer extends to the source contact and the drain contact.

15. The method of claim 11, wherein the nitride active structure comprises an aluminum gallium nitride (AlGaN)/gallium nitride (GaN) heterostructure.

16. The method of claim 11, wherein the sensing layer comprises the semiconductor layer and wherein the dielectric layer includes the at least one perforation.

17. The method of claim 16, wherein the dielectric layer further includes at least one perforation in the contact area adjacent to the contact for exposing the sensing layer to the medium.

* * * * *